(12) United States Patent
Stamm et al.

(10) Patent No.: US 7,078,574 B2
(45) Date of Patent: Jul. 18, 2006

(54) METHOD FOR THE INTRINSICALLY SAFE HANDLING OF 3-CHLOROPROPYNE

(75) Inventors: Armin Stamm, Nieder-Olm (DE); Heinz-Josef Kneuper, Niederkirchen (DE); Stefan Rittinger, Mannheim (DE); Peter Dransfeld, Albisheim (DE); Hans-Peter Schildberg, Neustadt (DE); Manfred Heilig, Ludwigshafen (DE); Theodor Weber, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 245 days.

(21) Appl. No.: 10/475,213

(22) PCT Filed: Apr. 17, 2002

(86) PCT No.: PCT/EP02/04249

§ 371 (c)(1),
(2), (4) Date: Oct. 20, 2003

(87) PCT Pub. No.: WO02/085824

PCT Pub. Date: Oct. 31, 2002

(65) Prior Publication Data

US 2004/0147791 A1 Jul. 29, 2004

(30) Foreign Application Priority Data

Apr. 21, 2001 (DE) .......................... 101 19 720

(51) Int. Cl.
*C07C 17/42* (2006.01)

(52) U.S. Cl. ..................... 570/108; 570/101; 570/102; 570/107; 62/606

(58) Field of Classification Search ................. 570/101, 570/102, 107, 108; 62/606
See application file for complete search history.

(56) References Cited

U.S. PATENT DOCUMENTS 2,926,204 A 2/1960 Wolfe
5,723,704 A 3/1998 Demail et al.
6,291,731 B1 * 9/2001 Stamm et al. ............... 570/217

FOREIGN PATENT DOCUMENTS

| DE | 1135 893 | 9/1962 |
|---|---|---|
| DE | 198 10 036 | 9/1999 |
| EP | 375 920 | 7/1990 |
| EP | 514 683 | 11/1992 |
| EP | 645 357 | 3/1995 |
| EP | 786 442 | 7/1997 |
| GB | 1132417 | 10/1968 |
| GB | 0795891 | * 9/2001 |
| WO | 99/64226 | 9/1999 |

OTHER PUBLICATIONS

Potential Hazards of Propargyl Halides and Allene, Forshey et al., 100–111.

Transport of Dangerous Goods, Manual of Tests and Criteria, 225–228.

European EN1839, CEN/TC 305/WG 1/SG 4:Explosion limits of gasea dn vapours, 31 pages, Jan. 2000.

Patent Abst. of Japan, 110 223 54, Aug. 8, 2000.

* cited by examiner

*Primary Examiner*—Johann Richter
*Assistant Examiner*—Lansana Nyalley
(74) *Attorney, Agent, or Firm*—Novan Druce Quigg; Jason D. Voight

(57) ABSTRACT

A method is provided for the intrinsically safe handling of 3-chloropropyne in the presence of a diluent with a boiling point ranging from −50° C. (223 K) to 200° C. (473 K) under atmospheric pressure, wherein the concentration of 3-chloropropyne in the liquid phase and in the gas phase is kept below the concentrations capable of deflagration by means of the type and amount of the diluent, the temperature and the total system pressure, together with the use of a 3-chloropropyne prepared, stored or transported in this way in the synthesis of dyestuffs, pharmaceutical and agricultural active ingredients, electroplating auxiliaries, disinfectants, steroids and growth hormones.

11 Claims, 4 Drawing Sheets

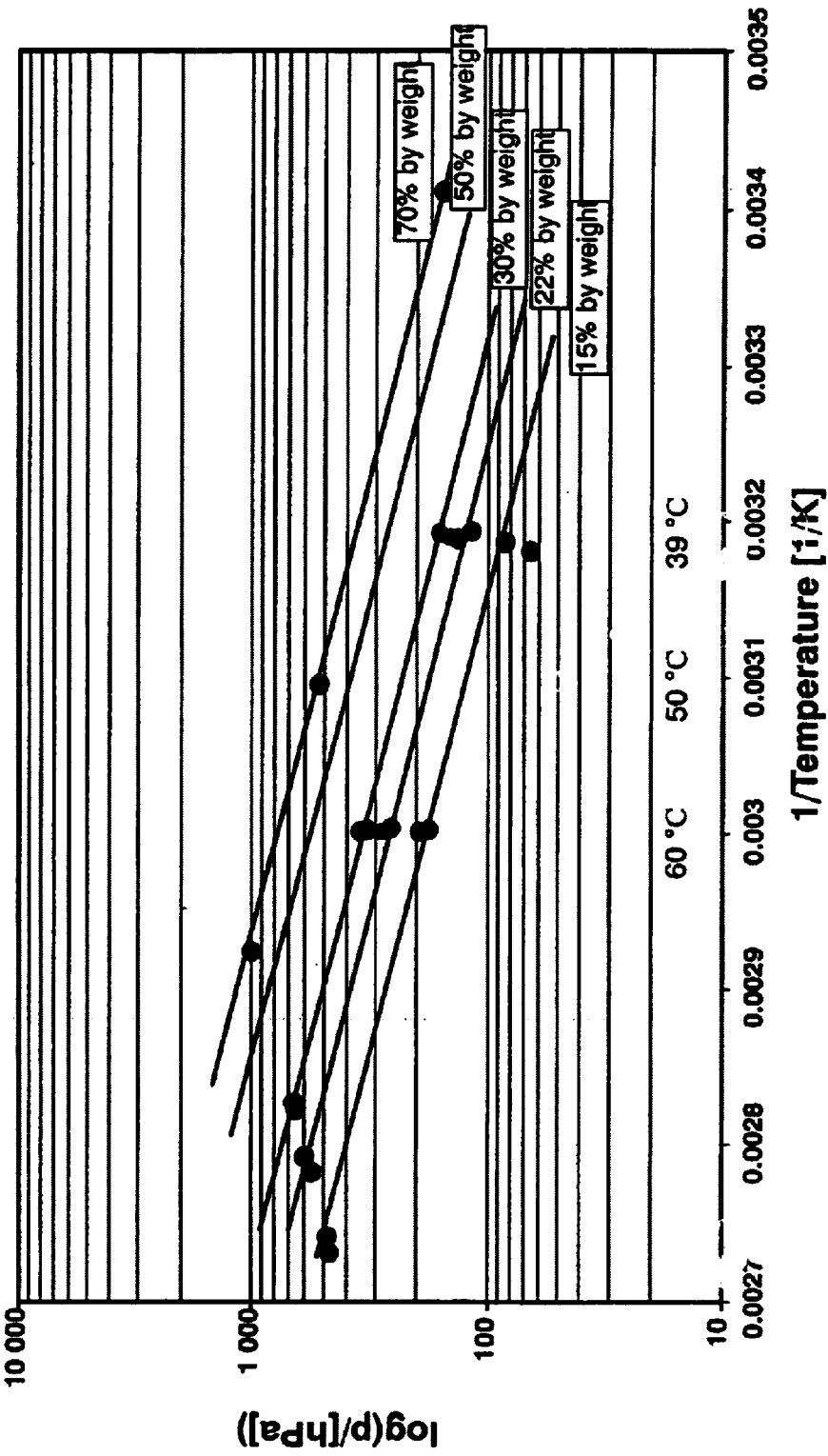
Figure 1: Temperature dependence of the 3-chloropropyne vapor pressure of mixtures containing different proportions [% by weight] of 3-chloropropyne with toluene as diluent

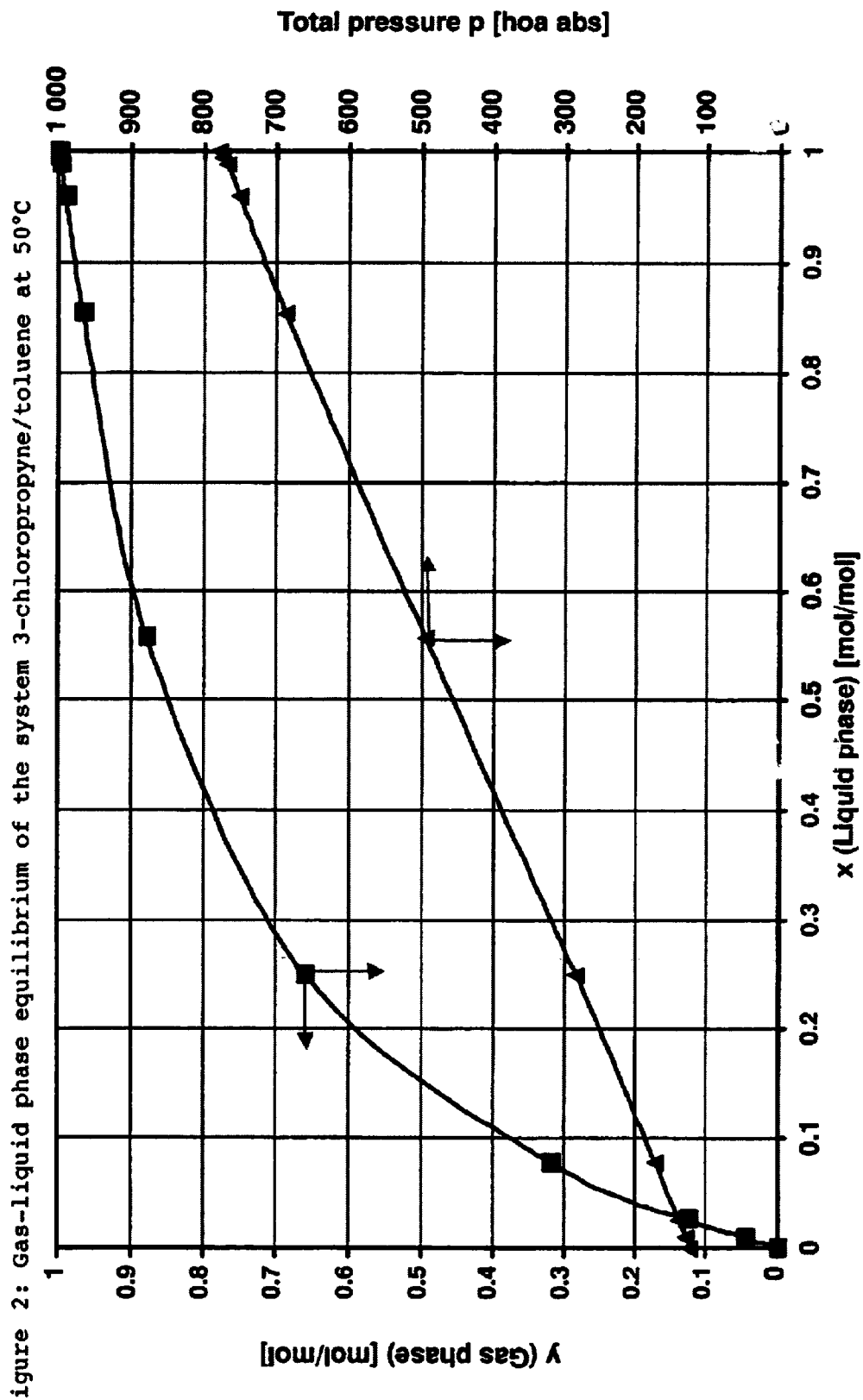
Figure 2: Gas-liquid phase equilibrium of the system 3-chloropropyne/toluene at 50°C

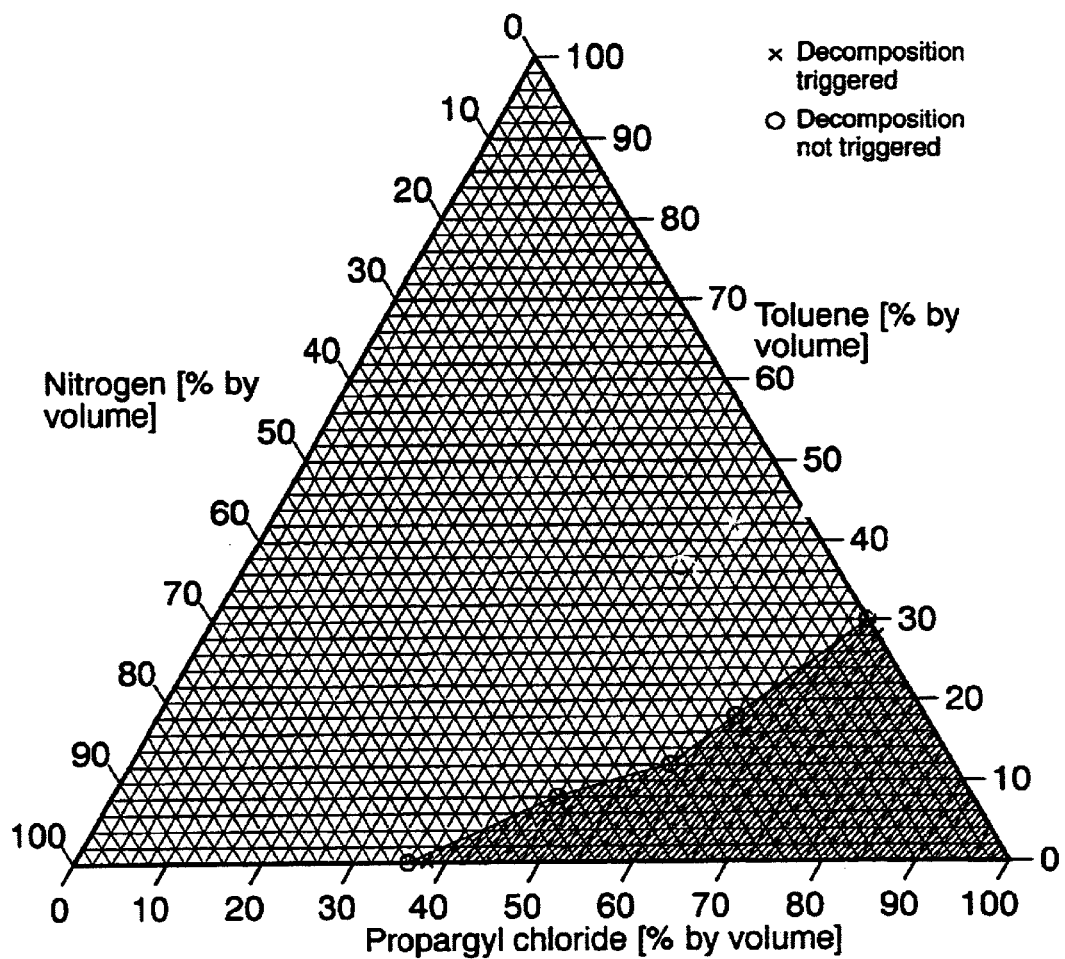
Figure 3a: Deflagration diagram of a gas mixture of 3-chloropropyne (propargyl chloride), toluene and nitrogen at 100°C and 0.10 MPa abs (cf. Table 6a)

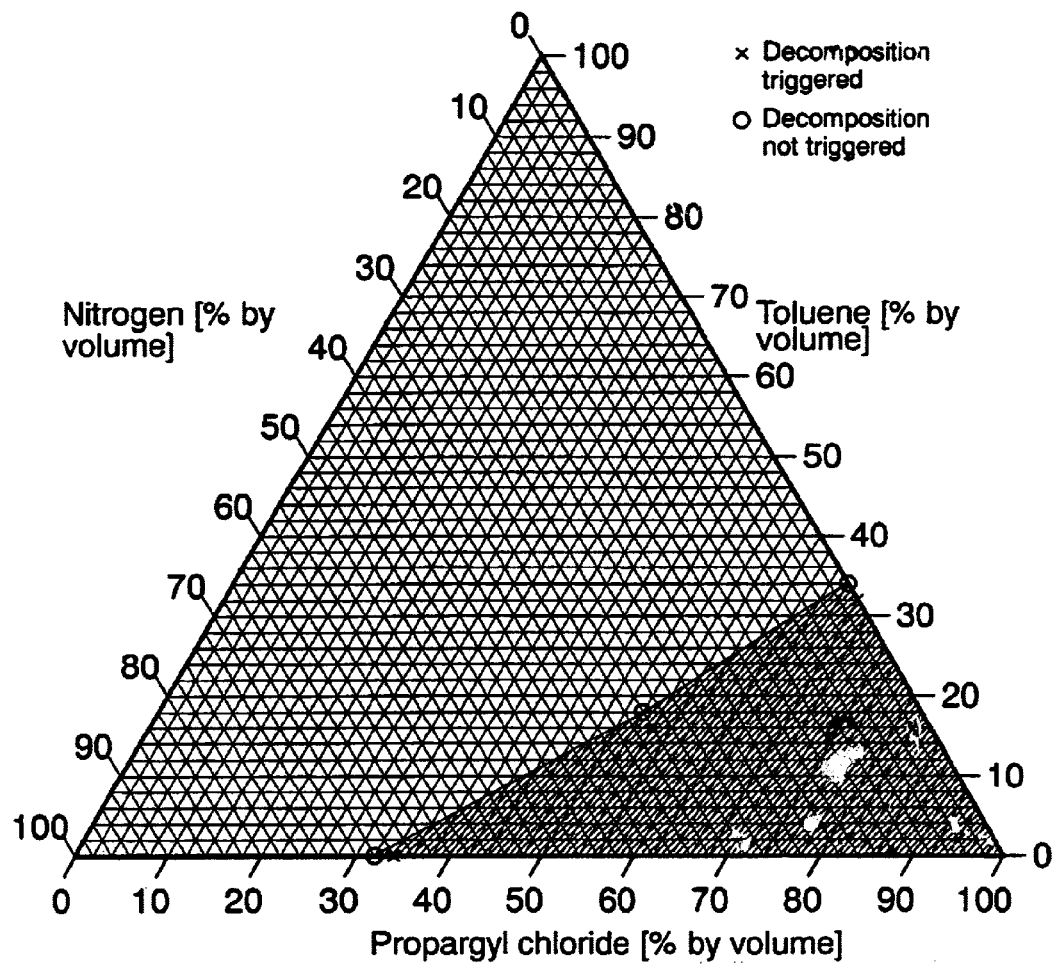
Figure 3b: Deflagration diagram of a gas mixture of 3-chloropropyne (propargyl chloride), toluene and nitrogen at 100°C (or 120°C) and 0.19 MPa abs (cf. Table 6b)

METHOD FOR THE INTRINSICALLY SAFE HANDLING OF 3-CHLOROPROPYNE

The present invention relates to a method for the intrinsically safe handling of 3-chloropropyne, especially its storage, its transportation and its preparation, in the presence of a diluent with a boiling point ranging from −50° C. (223 K) to 200° C. (473 K) under atmospheric pressure. The present invention further relates to the use of a 3-chloropropyne stored, transported and/or prepared in this way in the synthesis of dyestuffs, pharmaceutical and agricultural active ingredients, electroplating auxiliaries, disinfectants, steroids and growth hormones.

3-Chloropropyne (propargyl chloride) is an important intermediate in the synthesis of a large number of chemicals, especially dyestuffs, pharmaceutical and agricultural active ingredients, electroplating auxiliaries, disinfectants, steroids and growth hormones.

Aliphatic chloro compounds are generally prepared by reacting the appropriate alcohols with a chlorinating agent in the presence of a catalyst. The reaction of propyn-3-ol (propargyl alcohol) with phosgene ($COCl_2$) or thionyl chloride ($SOCl_2$) in the presence of catalysts is particularly suitable for the preparation of 3-chloropropyne on the industrial scale. The only coupling products formed in this process are the gaseous products hydrogen chloride and carbon dioxide or sulfur dioxide, which escape from the reaction mixture.

EP-A 0 786 442 describes a two-stage process for the preparation of alkyl chlorides from the corresponding alcohols. The first stage involves a reaction with hydrogen chloride and the second stage involves a reaction with phosgene in the presence of hexaalkylguanidinium halides, quaternary ammonium and phosphonium halides or pyridinium halides as catalyst, at a temperature of 80 to 160° C.

EP-A 0 375 920 teaches the preparation of alkyl and alkenyl chlorides by decarboxylation of the corresponding alkyl or alkenyl chloroformates in the presence of quaternary ammonium or phosphonium salts as catalyst, at a temperature of 50 to 200° C. and conventionally at 90 to 170° C. The alkyl or alkenyl chloroformates are prepared by reacting the appropriate alcohols with phosgene in an upstream synthesis stage or in situ.

German Auslegeschrift 1 135 893 describes the synthesis of propargyl chloride by reacting propargyl alcohol with phosgene in the presence of N,N-dialkyl-substituted carboxamides or N-alkyl-substituted lactams as catalyst. In this process the liquid catalyst is saturated with phosgene, after which propargyl alcohol and more phosgene are introduced.

EP-A 0 514 683 and EP-A 0 645 357 disclose processes for the preparation of alkynyl chlorides by reacting the appropriate alcohols with phosgene or thionyl chloride in the presence of a catalyst. According to EP-A 0 514 683 the chlorinating agent is added to a liquid phosphine oxide, after which the appropriate alcohol and more chlorinating agent are added. According to EP-A 0 645 357 the catalyst adduct is prepared first by introducing hydrogen chloride into N,N-disubstituted formamide, after which the appropriate alcohol is added and the chlorinating agent is introduced.

Offenlegungsschrift WO 99/46226 describes a continuous process for the preparation of propargyl chloride by reacting propargyl alcohol with a chlorinating agent in the presence of a catalyst and in the presence of a substituted aromatic hydrocarbon as diluent in an amount of 10 to 50% by weight, based on the amount of propargyl alcohol used.

It is known from the literature that 3-chloropropyne, in both the condensed phase and the gas phase, is prone to decomposition which progresses independently, even in the absence of oxygen (deflagration). Thus D. R. Forshey et al. in Fire Technology 5 (1969) pages 100 to 111 describe the sensitivity of pure liquid 3-chloropropyne to deflagration. A liquid stable to deflagration up to about 600 psig (about 4.3 MPa abs) is only obtained by adding 10% by weight of toluene. Pure gaseous 3-chloropropyne is sensitive to deflagration down to a pressure of 0.58 psia (4 kPa abs) at 25° C. The addition of 25% by volume of propane raises the deflagration limit to atmospheric pressure (0.1 MPa abs) and 48° C.

It was recognized according to the invention that the processes described carry a high safety risk due to the presence of at least one phase capable of deflagration (liquid phase and/or gas phase) and that ignition, for example by a static discharge, can cause considerable damage to people and property. In the process according to the teaching of German Auslegeschrift 1 135 893, both the liquid phase and the gas phase are capable of deflagration because of the high concentrations of 3-chloropropyne which develop. In the process according to the teaching of WO 99/46226, although a liquid phase stable to deflagration is obtained by using a substituted aromatic hydrocarbon as diluent, the gas phase which exists in thermodynamic equilibrium is definitely capable of deflagration.

It is an object of the present invention to find a method for the handling, especially for the preparation, storage and transportation, of 3-chloropropyne which no longer exhibits the abovementioned disadvantages, is inexpensive and simple to carry out in terms of process engineering and also carries no risk of deflagration in the presence of potential sources of ignition.

We have found that this object is achieved by a method for the intrinsically safe handling of 3-chloropropyne in the presence of a diluent with a boiling point ranging from −50° C. (223 K) to 200° C. (473 K) under atmospheric pressure, wherein the concentration of 3-chloropropyne in the liquid phase and in the gas phase is kept below the concentrations capable of deflagration by means of the type and amount of the diluent, the temperature and the total system pressure.

The handling of 3-chloropropyne is said to be intrinsically safe when the criterion of stability to deflagration of the liquid phase and the gas phase in thermodynamic equilibrium is satisfied at a given temperature and a given total system pressure.

A concentration capable of deflagration is understood as meaning a concentration of 3-chloropropyne, in the particular phase in question, at which a deflagration, i.e. a decomposition of 3-chloropropyne which progresses independently, can be triggered by using a source of ignition.

The deflagrability of the liquid phase is determined on the basis of deflagration test "C.2" described on pages 225 to 228 under section 23.4.2 of "Recommendations on the Transport of Dangerous Goods—Manual of Tests and Criteria", $3^{rd}$ revised edition, United Nations, New York and Geneva 1999, ISBN 92-1-139068-0. The determination is performed at the desired temperature and the desired pressure in a 300 ml Dewar vessel with an internal diameter of 48±1 mm, filled to about 20 mm below the rim with the liquid to be measured. The source of ignition to be used for the liquid phase is a gas flame with a minimum length of 20 mm, directed onto the liquid surface. Any deflagration triggered by the ignition is determined via the rate of propagation of the generated temperature wave. This is done by placing a thermocouple in the Dewar vessel at distances of 50 and 100 mm below the rim and recording the temperatures as a function of time. If the measured propagation rate of the temperature wave is ≧0.35 mm/s, the liquid phase is considered to be capable of deflagration. If the value is <0.35 mm/s, the liquid phase is considered to be incapable of deflagration.

The deflagrability of the gas phase is determined according to future European standard prEN1839, Method B "bomb method" (working document of the Physikalisch Technische Bundesanstalt Braunschweig entitled "CEN/TC 305/WG1/SG 4", January 2000) in a cylindrical or spherical container with a gas phase volume of at least 5 l, the diameter being at least 80 mm in the case of a cylindrical container. A platinum wire melting on ignition, between two metal rods, is to be used as the source of ignition for the gas phase. The metal rods should be made of stainless steel and be arranged parallel to one another. Their ends should be separated by 5±1 mm and be located in the middle of the container. The platinum wire should have a diameter of 0.05 to 0.2 mm. The voltage and current are to be adjusted so as to result in an ignition energy of 10 to 100 J. Any deflagration triggered by the ignition is to be detected via the increase in the pressure inside the container as a function of time. The criterion used for a deflagration is the maximum absolute pressure measured in the container after ignition. If this is more than 1.05 times the initial pressure before ignition, the gas mixture is considered to be capable of deflagration. If it is 1.05 times the initial pressure before ignition, or less, the gas mixture is considered to be incapable of deflagration.

The deflagrability of the liquid phase and the gas phase is crucially dependent on their composition, temperature and total pressure. As is generally known and described in the literature, pure 3-chloropropyne, in both the liquid phase and the gas phase, is capable of deflagration over a wide temperature and pressure range.

An essential feature of the method according to the invention is that the concentration of 3-chloropropyne in both the liquid phase and the gas phase is kept below the concentrations capable of deflagration by means of the type and amount of the diluent, the temperature and the total system pressure, so that both the liquid phase and the gas phase are stable to deflagration.

By adjustment of the thermodynamic equilibrium between the liquid phase and the gas phase above it, the concentration of 3-chloropropyne is regulated so that it is below the concentration capable of deflagration in both phases. On purely thermodynamic grounds, a 3-chloropropyne concentration above the concentration capable of deflagration cannot be obtained at any location in the system. Thus, for example, the maximum amount of 3-chloropropyne subsequently furnished from the liquid phase is not sufficient to create a phase capable of deflagration.

In contrast, in a procedure not according to the invention, at least one phase would be capable of deflagration due to an insufficient addition of a diluent after adjustment of the thermodynamic equilibrium, since the concentration of 3-chloropropyne is above the concentration capable of deflagration. Thus, as already described in the introduction, in a process according to the teaching of WO 99/46226, although a liquid phase stable to deflagration is obtained, a gas phase stable to deflagration is not, since the amount of 3-chloropropyne subsequently furnished from the liquid phase because of the thermodynamic equilibrium is such that the concentration attained in the gas phase is above the concentration capable of deflagration. Although an additional continuous or intermittent supply of another gaseous component, for example a continuous or intermittent flushing with an inert gas (e.g. nitrogen) or a continuous or intermittent formation of reaction off-gases (e.g. carbon dioxide and hydrogen chloride in the preparation of 3-chloropropyne from propyn-3-ol and phosgene in the presence of a catalyst), could keep the concentration of 3-chloropropyne in the gas phase below the concentration capable of deflagration due to perturbation of the thermodynamic equilibrium, this does not constitute intrinsically safe handling within the framework of the present invention. Thus, for example, if the source of supply of the other gaseous component were to dry up, the thermodynamic equilibrium would re-establish itself and the 3-chloropropyne concentration would thus also rise above the concentration capable of deflagration.

In the method according to the invention, it is possible and as a rule even advantageous for the sum of the partial pressures of 3-chloropropyne and diluent in the gas phase to be lower than the desired total system pressure because of the thermodynamic equilibrium. In this case the pressure balance between the desired total system pressure and the partial pressures of 3-chloropropyne and diluent is compensated by the presence of at least one other gaseous component. Through this advantageous option the method according to the invention gains an additional degree of freedom inasmuch as both the temperature and the total system pressure can be varied for a given type and amount of diluent. Without another gaseous component, the total system pressure would be thermodynamically fixed for a given temperature and the temperature would be thermodynamically fixed for a given total system pressure.

Because all four of said parameters (type of diluent, amount of diluent, temperature and total system pressure) exercise a decisive influence on the deflagrability of both phases, they have to be fixed with care. If no data are available, for example in the form of phase diagrams and deflagration diagrams, these should generally be determined experimentally. The practical procedure for fixing the parameters and determining the required data is generally as follows.

For practical considerations the parameter ranges are normally preset for the temperature and the total system pressure. 3-Chloropropyne will generally be handled in a temperature range of −50° C. (223 K) to 200° C. (473 K) and at a total pressure of 0.01 to 5 MPa abs. As starting values for the following determinations, it is advantageous to choose a temperature value and a total pressure value at which it is desired to handle the 3-chloropropyne. It is additionally necessary to choose the desired diluent (referred to above as "type of diluent"). Relevant criteria for choosing the diluent are described at a later stage.

Once the temperature, total system pressure and diluent type have been decided, the amount of diluent desired for the following data determinations is chosen and an appropriate system is set up experimentally. If the presence of at least one other component in the gas phase is required for adjusting the total pressure to the desired value (see above), said component is to be added to the system. As far as is practically possible, the experimental system should contain all the components of the ultimate industrial system, for example by-products or catalysts. If the preparation of 3-chloropropyne is involved, it is generally advantageous to adhere as closely as possible to the practical conditions for determination of the data.

The deflagrability of the liquid phase is advantageously determined by taking a sample and measuring the deflagrability of the liquid phase as described above (on the basis of deflagration test "C.2", "Recommendations on the Transport of Dangerous Goods—Manual of Tests and Criteria", 3$^{rd}$ revised edition, United Nations, New York and Geneva 1999, ISBN 92-1-139068-0, pages 225 to 228, section 23.4.2). Alternatively, the deflagrability of the liquid phase can also be measured using a separately prepared mixture which has the same composition as the liquid phase to be measured.

The deflagrability of the gas phase is advantageously determined by taking a sample and measuring the deflagrability of the gas phase as described above (standard prEN1839, Method B "bomb method", working document of Physikalisch Technische Bundesanstalt Braunschweig entitled "CEN/TC 305/WG1/SG 4", January 2000). Alternatively, the deflagrability of the gas phase can also be measured using a separately prepared mixture which has the same composition as the gas phase to be measured. A further possibility is to determine the composition of the gas phase via experimental or tabulated data of the thermodynamic equilibrium between the gas and liquid phases from the chosen liquid phase composition.

The result of the above measurements provides evidence as to whether or not the liquid phase and/or the gas phase is/are capable of deflagration under the chosen conditions. It is based on a concrete set of parameters without knowledge of their effects on the deflagrability in the event of smaller or larger deviations, especially in the position of the deflagration limit. The deflagration limit is understood as meaning the transition between being capable and incapable of deflagration when varying at least one parameter, for example the composition of the liquid or gas phase, the temperature or the total system pressure.

To obtain evidence about the deflagrability in the event of smaller or larger deviations in the set parameters as well, it is therefore advantageous to vary individual parameters and carry out further determinations on deflagrability. In the preparation of 3-chloropropyne, the progress of the reaction is also to be understood as a parameter in this sense because the composition of the liquid phase and the gas phase can change in the course of the reaction.

The result of such measurements ultimately gives an overview of the sensitivity of the system to deflagration when the parameters vary. It provides evidence as to whether or not the system is still intrinsically safe when the parameter variations to be expected are taken as a basis. To create a safety reserve, it is advantageous to adjust the concentration of 3-chloropropyne in the liquid phase and the gas phase in such a way that the limit for a system capable of deflagration is not attained within the expected range of parameter variations.

The diluents used in the method according to the invention have a boiling point ranging from −50° C. (223 K) to 200° C. (473 K) under atmospheric pressure. The diluents can be organic or inorganic compounds. They should be chemically inert to 3-chloropropyne. If the method according to the invention is used in the preparation of 3-chloropropyne, the diluents should also be chemically inert to the educt used, the chlorinating agent and any catalyst required. "Chemically inert" means that the diluents do not react chemically with said substances under the chosen conditions. The diluents used are preferably completely miscible with 3-chloropropyne under the chosen conditions.

The diluents usable in the method according to the invention can be for example aliphatic, aromatic or araliphatic, saturated or unsaturated, unsubstituted or substituted hydrocarbons. The hydrocarbons can contain one or more heteroatoms, for instance oxygen, nitrogen, sulfur or phosphorus, examples being —O—, —S—, —SO—, —SO$_2$—, —NH—, —NR—, —CO—, —PR—, —P(O)R— and/or —N═, in aliphatic or aromatic systems. They can also be substituted by one or more functional groups containing for example oxygen, nitrogen, sulfur and/or halogen, such as —COOR, —F, —Cl, —Br, —I and/or —CN. Inorganic diluents which may be mentioned are sulfur dioxide or carbon dioxide liquefied under superatmospheric pressure. The method according to the invention can also be carried out with a mixture of different diluents.

Examples of the preferred diluents which may be mentioned are unbranched and branched C$_3$- to C$_{11}$-alkanes, for example propane, n-butane, isobutane (2-methylpropane), n-pentane, 2-methylbutane (isopentane), 2,2-dimethylpropane, n-hexane, 2-methylpentane, 3-methylpentane, 2,3-dimethylbutane, 2,2-dimethylbutane, n-heptane, isomeric heptanes, n-octane, isomeric octanes, n-nonane, isomeric nonanes, n-decane, isomeric decanes, n-undecane and isomeric undecanes;

unbranched and branched C$_5$- to C$_{12}$-cycloalkanes with one or two optionally fused 5-membered to 8-membered rings, for example cyclopentane, cyclohexane, cycloheptane, cyclooctane, methylcyclopentane, methylcyclohexane and decahydronaphthalene (decalin);

benzene and C$_1$- to C$_4$-alkyl-substituted benzenes having a total of 7 to 10 carbon atoms, for example toluene, o-xylene, m-xylene, p-xylene, ethylbenzene, 1,3,5-trimethylbenzene (mesitylene), 1,2,4-trimethylbenzene, 2-ethyltoluene, 3-ethyltoluene, 4-ethyltoluene, propylbenzene, isopropylbenzene (cumene), 1,2,4,5-tetramethylbenzene, 1,2-diethylbenzene, 1,4-diethylbenzene, butylbenzene, isobutylbenzene (2-methyl-1-phenylpropane), sec-butylbenzene (2-phenylbutane) and tert-butylbenzene (2-methyl-2-phenylpropane);

aliphatic or araliphatic ethers having a total of 2 to 10 carbon atoms, for example dimethyl ether, diethyl ether, methyl tert-butyl ether, dipropyl ether, diisopropyl ether, n-butyl ethyl ether, ethyl tert-butyl ether, methyl tert-pentyl ether, dibutyl ether, dipentyl ether, 1,2-dimethoxyethane (ethylene glycol dimethyl ether), 1,2-diethoxyethane (ethylene glycol diethyl ether), bis (2-methoxyethyl) ether (diethylene glycol dimethyl ether), bis(2-ethoxyethyl) ether (diethylene glycol diethyl ether), tetrahydrofuran, 1,4-dioxane and anisole (methoxybenzene);

aliphatic or araliphatic esters having a total of 2 to 10 carbon atoms, for example methyl formate, ethyl formate, propyl formate, butyl formate, pentyl formate, hexyl formate, 2-ethylhexyl formate, methyl acetate, ethyl acetate, propyl acetate, butyl acetate, pentyl acetate, hexyl acetate, 2-ethylhexyl acetate, methyl propionate, ethyl propionate, propyl propionate, butyl propionate, pentyl propionate, hexyl propionate, methyl butyrate, ethyl butyrate, propyl butyrate, butyl butyrate, pentyl butyrate and hexyl butyrate;

halogenated aliphatic, aromatic or araliphatic hydrocarbons having from 1 to 10 carbon atoms, for example chloromethane, dichloromethane, trichloromethane, tetrachloromethane, 1,2-dichloroethane and chlorobenzene, preferably having 1 to 3 carbon atoms, for example chloromethane, dichloromethane, trichloromethane and 1,2-dichloroethane;

or mixtures thereof.

In the method according to the invention, the diluent is generally used in an amount of 1 to 2 000% by weight in the liquid phase, based on the amount of 3-chloropropyne.

In one of the preferred variants of the method according to the invention, a diluent is used which boils at the same temperature as 3-chloropropyne or above. According to the literature, 3-chloropropyne boils at about 57° C. under atmospheric pressure. The upper limit of the boiling point of said diluent is 200° C. (473 K), as already stated. It is particularly preferred to use a diluent whose boiling point ranges from that of 3-chloropropyne to 150° C. (423 K) under atmospheric pressure.

The diluent of this preferred variant, which boils at the same temperature as 3-chloropropyne or above, is used in an amount preferably of 50 to 2 000% by weight and particularly preferably of 50 to 1 000% by weight in the liquid phase, based on the amount of 3-chloropropyne in the liquid phase.

In this preferred variant of the method according to the invention, the diluents used, which boil at the same temperature as 3-chloropropyne or above, are particularly preferably an unbranched or branched $C_6$- to $C_8$-alkane, for example n-hexane, 2-methylpentane, 3-methylpentane, 2,3-dimethylbutane, 2,2-dimethylbutane, n-heptane, isomeric heptanes, n-octane and isomeric octanes, especially n-hexane, 2-methylpentane and isomeric heptanes;

an unbranched or branched $C_6$- to $C_8$-cycloalkane with a 5-membered or 6-membered ring, for example cyclopentane, cyclohexane, cycloheptane, cyclooctane, methylcyclopentane and methylcyclohexane, especially cyclopentane and cyclohexane;

benzene, toluene, ethylbenzene and xylenes (specifically o-xylene, m-xylene and p-xylene), especially toluene;

or mixtures thereof.

In another of the preferred variants of the method according to the invention, a mixture of (a) a diluent boiling at the same temperature as 3-chloropropyne or above, and (b) a diluent boiling below 3-chloropropyne, is used. According to the literature, 3-chloropropyne boils at about 57° C. under atmospheric pressure. The upper limit of the boiling point of the diluent mentioned under (a) is 200° C. (473 K), as already stated. The lower limit of the boiling point of the diluent mentioned under (b) is −50° C. (223 K), as already stated. As the diluent mentioned under (a), it is particularly preferred to use a diluent whose boiling point ranges from that of 3-chloropropyne to 150° C. (423 K) under atmospheric pressure.

The diluent of this preferred variant, which boils at the same 45 temperature as 3-chloropropyne or above, is used in an amount preferably of 1 to 1 000% by weight, particularly preferably of 1 to 100% by weight and very particularly preferably of 1 to 20% by weight in the liquid phase, based on the amount of 3-chloropropyne in the liquid phase. The diluent of this preferred variant which boils below 3-chloropropyne is used in an amount preferably of 1 to 500% by weight and particularly preferably of 5 to 250% by weight in the liquid phase, based on the amount of 3-chloropropyne in the liquid phase.

As regards examples of the preferred diluents among those mentioned under (a), which boil at the same temperature as 3-chloropropyne or above, reference may be made to the above list in the description of the previously mentioned variant of the method according to the invention.

In this preferred variant of the method according to the invention, the diluents (a) used, which boil at the same temperature as 3-chloropropyne or above, are particularly preferably an unbranched or branched $C_6$- to $C_8$-alkane, for example n-hexane, 2-methylpentane, 3-methylpentane, 2,3-dimethylbutane, 2,2-dimethylbutane, n-heptane, isomeric heptanes, n-octane and isomeric octanes, especially n-hexane, 2-methylpentane, 3-methylpentane and isomeric heptanes;

an unbranched or branched $C_6$- to $C_8$-cycloalkane with a 5-membered or 6-membered ring, for example cyclopentane, cyclohexane, cycloheptane, cyclooctane, methylcyclopentane and methylcyclohexane, especially cyclopentane and cyclohexane;

benzene, toluene, ethylbenzene and xylenes (specifically o-xylene, m-xylene and p-xylene), especially toluene;

or mixtures thereof, and the diluents (b) used, which boil below 3-chloropropyne, are particularly preferably an unbranched or branched $C_3$- to $C_5$-alkane, for example propane, n-butane, isobutane (2-methylpropane), n-pentane, 2-methylbutane (isopentane) and 2,2-dimethylpropane, especially propane, isobutane (2-methylpropane) and n-pentane;

cyclopentane;

an aliphatic ether having a total of 2 to 5 carbon atoms, for example dimethyl ether, diethyl ether, methyl tert-butyl ether, 1,2-dimethoxyethane (ethylene glycol dimethyl ether), tetrahydrofuran and 1,4-dioxane, especially dimethyl ether, diethyl ether and methyl tert-butyl ether;

chloromethane;

or mixtures thereof.

The combined use of a diluent boiling at the same temperature as 3-chloropropyne or above with a diluent boiling below 3-chloropropyne has the advantage of assuring intrinsically safe handling with a smaller total amount of diluent than for example when using only one diluent boiling at the same temperature as 3-chloropropyne or above. The lower boiling diluent is particularly effective at lowering the concentration of 3-chloropropyne in the gas phase, and the diluent boiling at the same temperature or above is particularly effective at lowering the concentration of 3-chloropropyne in the liquid phase.

As already described previously, in the method according to the invention, it is possible and as a rule even advantageous for the sum of the partial pressures of 3-chloropropyne and diluent in the gas phase to be lower than the desired total system pressure because of the thermodynamic equilibrium, and hence for the pressure balance to be compensatable by the presence of at least one other gaseous component. The pressure balance between the total system pressure and the partial pressure of 3-chloropropyne and the partial pressure of the diluent is preferably compensated by the presence of an inert gas.

Inert gases are understood as meaning substances whose boiling or sublimation point is below −50° C. (223 K) under atmospheric pressure and which are chemically inert to 3-chloropropyne, i.e. do not react chemically with 3-chloropropyne under the chosen conditions.

Examples of suitable inert gases which may be mentioned are helium, neon, argon, krypton, xenon, nitrogen, carbon monoxide, carbon dioxide, methane, ethane, ethene, hydrogen chloride and mixtures thereof. Preferred inert gases which may be mentioned are methane, nitrogen, carbon monoxide, carbon dioxide, hydrogen chloride and mixtures thereof.

In the method according to the invention, the system is kept at a temperature ranging preferably from −20° C. (253 K) to 100° C. (373 K) and particularly preferably from 0° C. (273 K) to 100° C. (373 K).

The total system pressure is kept preferably at 0.05 to 1 MPa abs and particularly preferably at 0.05 to 0.5 MPa abs.

One of the preferred variants of the method according to the invention is to store or transport the 3-chloropropyne. The storage and transportation time is normally irrelevant in the methods according to the invention. It can be a few minutes to several years. The time generally ranges from a few hours to several months. 3-Chloropropyne is generally stored and transported using containers. Their size is normally irrelevant in the method according to the invention. Containers in the 1 to m³ range are used as a rule.

3-Chloropropyne is stored and transported at a temperature preferably of 0° C. (273 K) to 100° C. (373 K) and particularly preferably of 0° C. (273 K) to 50° C. (323 K). The total system pressure is preferably 0.05 to 0.5 MPa abs and particularly preferably 0.09 to 0.2 MPa abs. In particular, 3-chloropropyne is stored and transported under atmospheric pressure.

Another of the preferred variants of the method according to the invention is to prepare the 3-chloropropyne by reacting propyn-3-ol with a chlorinating agent, optionally in the presence of a catalyst.

The chlorinating agent used is generally phosgene, trichloromethyl chloroformate (diphosgene), bis(trichloromethyl) carbonate (triphosgene), thionyl chloride or phosphorus trichloride, preferably phosgene. Phosgene can be added in gaseous or liquid form in the method according to the invention. When using phosgene, trichloromethyl chloroformate (diphosgene), bis(trichloromethyl) carbonate (triphosgene) and thionyl chloride, the presence of a catalyst is generally required. When using phosphorus trichloride, the presence of a catalyst is optional.

In principle, the catalysts used in the method according to the invention can be any conventional known catalysts for the chlorination of carboxylic acids and alcohols. Examples which may be mentioned are N,N-disubstituted formamides, especially N,N-disubstituted formamides of the general formula (I):

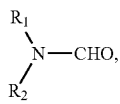

in which $R^1$ and $R^2$ independently of one another are $C_1$- to $C_8$-alkyl or $R^1$ and $R^2$ together are a $C_4$- or $C_5$-alkylene chain which can optionally be interrupted by one or more oxygen or nitrogen atoms, for example N,N-dimethylformamide, N,N-diethylformamide, N,N-dipropylformamide, N,N-diisopropylformamide, N,N-dibutylformamide, N,N-di-sec-butylformamide, N,N-diisobutylformamide, N,N-dipentylformamide, N,N-dihexylformamide, N,N-dioctylformamide, N-formylpyrrolidine and N-formylpiperidine;

tetraalkyl-substituted ureas, especially tetra-$C_1$- to $C_4$-alkyl-substituted ureas, for example tetramethylurea, tetraethylurea and tetrabutylurea;

alicyclic N,N'-alkyl- or aryl-substituted ureas, especially alicyclic N,N'-$C_1$- to $C_4$-alkyl-substituted ureas with a 5-membered or 6-membered ring system, for example dimethylethyleneurea (N,N'-dimethyl-2-imidazolidinone) and dimethylpropyleneurea (N,N'-dimethyltetrahydro-2(1H)-pyrimidinone);

tetraalkylamidinium salts, especially tetra-$C_1$- to $C_4$-alkylformamidinium salts, for example tetramethylformamidinium chloride;

hexaalkylguanidinium salts, especially hexa-$C_1$- to $C_4$-alkylguanidinium salts, for example N,N,N',N',N'',N''-hexamethylguanidinium chloride and N,N,N',N',N'',N''-hexabutylguanidinium chloride;

trialkyl- or triarylphosphine oxides, especially tri-$C_1$- to $C_8$-alkylphosphine oxides or triarylphosphine oxides, for example triphenylphosphine oxide and tri-$C_6$- to $C_8$-alkylphosphine oxide mixtures (e.g. "Cyanex®923" from Cytec Industries);

pyridine or its alkyl-substituted derivatives, especially mono-$C_1$-$C_4$-alkylpyridines, for example 2-methylpyridine (α-picoline), 3-methylpyridine (β-picoline) and 4-methylpyridine (γ-picoline); and N-alkylimidazoles, especially N—$C_1$- to $C_4$-alkylimidazoles, for example N-methylimidazole.

The amount of catalyst is generally 0.1 to 20 mol % and preferably 0.5 to 10 mol %, based on the amount of propyn-3-ol used.

The reaction with the chlorinating agent is generally carried out at a temperature of 0 to 150° C., preferably of 20 to 100° C. and very particularly preferably of 40 to 70° C. It is generally carried out under a pressure of 0.01 to 5 MPa abs, preferably of 0.05 to 0.2 MPa abs and particularly preferably of 0.08 to 0.15 MPa abs, especially under atmospheric pressure.

The reaction with the chlorinating agent can be carried out batchwise or continuously.

In one particularly preferred variant for the preparation of 3-chloropropyne by the method according to the invention, the chlorinating agent used is phosgene and the catalyst used is an N,N-disubstituted formamide of the general formula (I):

in which $R^1$ and $R^2$ independently of one another are $C_1$— to $C_8$-alkyl or $R^1$ and $R^2$ together are a $C_4$- or $C_5$-alkylene chain which can optionally be interrupted by one or more oxygen or nitrogen atoms, especially N,N-dimethylformamide, N,N-diethylformamide, N,N-dipropylformamide, N,N-diisopropylformamide, N,N-dibutylformamide, N,N-di-sec-butylformamide or N,N-diisobutylformamide.

When the N,N-disubstituted formamide used is reacted with the chlorinating agent, the so-called Vilsmeier adduct is formed as the chlorinating reagent which is actually reactive.

In the preparation of 3-chloropropyne, it is also advantageous for safety reasons to suppress the formation of propargyl chloroformate by ensuring that the concentration of catalyst and phosgene in the reaction system is sufficiently high, because propargyl chloroformate can decompose spontaneously to eliminate carbon dioxide and release a substantial amount of energy.

In one general embodiment for the intrinsically safe storage or intrinsically safe transportation of 3-chloropropyne, the 3-chloropropyne is mixed with a suitable diluent in an amount which, at the desired temperature and under the desired pressure, is sufficient to keep the liquid phase and the gas phase stable to deflagration. If necessary, another gaseous component is to be added in order to restore the pressure balance between the desired total system pressure and the sum of the partial pressures of 3-chloropropyne and diluent.

In one preferred embodiment for the intrinsically safe storage or intrinsically safe transportation of 3-chloropropyne, a mixture of 15 to 30% by weight of 3-chloropropyne and 85 to 70% by weight of toluene is placed in a container previously filled with an inert gas, preferably nitrogen. This generally sealed container, with a preferred initial internal pressure of about one atmosphere at the filling temperature, can then be stored and/or transported at the conventional temperatures, preferably at 0 to 50° C., without a liquid phase capable of deflagration or a gas phase capable of deflagration being able to form inside.

In one general embodiment for the batch preparation of 3-chloropropyne, the desired total amount of propyn-3-ol together with the appropriate amount of a suitable diluent, and the desired catalyst, are placed in a reaction vessel. The heating of the mixture to the desired reaction temperature is then started and the amount of chlorinating agent, preferably phosgene, required to convert the propyn-3-ol is introduced with intense thorough mixing. When the introduction of the chlorinating agent has ended, the reaction is optionally allowed to continue for a few minutes to a few hours longer.

In one preferred embodiment for the continuous preparation of 3-chloropropyne, the reaction is started up by placing a small amount of propyn-3-ol together with the appropriate amount of a suitable diluent, and the desired catalyst, in a reaction vessel. The heating of the mixture to the desired reaction temperature is then started and the amount of phosgene required to convert the propyn-3-ol is introduced with intense thorough mixing. Alternatively, it is also possible to place a small amount of 3-chloropropyne together with the appropriate amount of a suitable diluent, and the desired catalyst, in a reaction vessel, heat the mixture to the desired reaction temperature and start adding the phosgene. The starting solution, containing propyn-3-ol, diluent and catalyst, and the required amount of phosgene, are then introduced continuously and in parallel. When a specific amount of starting solution has been introduced, or a specific liquid level has been reached in the reaction vessel, the addition of phosgene is stopped. The starting solution is normally introduced until the off-gas stream of hydrogen chloride and carbon dioxide formed dries up, i.e. until the phosgene present in solution has been converted. The crude solution obtained is then cooled and transferred to a storage container.

We have also found that 3-chloropropyne prepared, stored and/or transported by the method according to the invention can be used in the synthesis of dyestuffs, pharmaceutical and agricultural active ingredients, electroplating auxiliaries, disinfectants, steroids and growth hormones.

The method according to the invention affords the intrinsically safe handling of 3-chloropropyne by ensuring that the liquid phase and the gas phase are stable to deflagration through the presence of a diluent. The stability to deflagration of both phases is assured by the type and amount of the diluent, the temperature and the total system pressure. By virtue of this assurance, already achieved by adjustment of the thermodynamic equilibrium between the two phases, a 3-chloropropyne concentration above the concentration capable of deflagration cannot be obtained at any location in the system.

In particular, the method according to the invention enables 3-chloropropyne to be stored, transported and prepared at a very high safety level.

EXAMPLES

Experimental Procedure 1: Determination of the Gas Phase Concentration of 3-chloropropyne as a Function of the Liquid Phase Concentration The experiments for determination of the gas phase concentration of 3-chloropropyne as a function of the liquid phase concentration were performed in a circulation apparatus for the dynamic determination of gas-liquid phase equilibrium data. Liquid mixtures of 3-chloropropyne and a diluent, and optionally N,N-diisobutylformamide (DIBF), were placed in the apparatus and the gas-liquid phase equilibrium was adjusted, measurements being made of the vapor pressure resulting at a given temperature and the boiling point resulting at a given pressure. Samples were taken from the liquid phase and from the previously condensed gas phase for gas chromatographic analysis. The gas chromatographic analyses were used to calculate the partial pressures of 3-chloropropyne and diluent.

Experimental Procedure 2: Determination of the Deflagration Limit of Gas Mixtures Containing 3-chloropropyne The experiments for determination of the deflagration limit of gas mixtures, i.e. the boundary line between the compositions of the gas mixtures at which on the one hand an independently progressing decomposition can be triggered and at which on the other hand an independently progressing decomposition cannot be triggered, were performed on the basis of future European standard prEN1839, Method B "bomb method", in a spherical heatable 5 l high-pressure vessel (working document of the Physikalisch Technische Bundesanstalt Braunschweig entitled "CEN/TC 305/WG1/SG 4", January 2000).

The gas mixtures were prepared by the partial pressure method. Assuming ideal behavior, this means that the pressure increase in the vessel caused by the addition of each component corresponds to the partial pressure of this component in the overall mixture, and that the proportion of the total pressure made up of the partial pressure of a component is identical to its proportion by volume and its molar proportion.

The gases were mixed thoroughly for approx. 5 minutes with a magnetic propeller stirrer. Ignition was effected with a fusing wire, the melting of which is followed by the appearance of an arc (cf. future European standard prEN1839, Method B "bomb method", "fusing wire"). The ignition energy released was approx. 70 J. Any independent propagation of a reaction front (deflagration) initiated by the ignition was detected via a piezoelectric measurement as the pressure inside the vessel increased with time. The criterion used for a deflagration was the maximum absolute pressure measured in the vessel after ignition. If this was more than 1.05 times the initial pressure before ignition, the gas mixture was classed as capable of deflagration. If it was 1.05 times the initial pressure before ignition, or less, the gas mixture was classed as incapable of deflagration.

Example 1

Determination of the Gas Phase Concentration and Vapor Pressure of 3-chloropropyne as a Function of the Liquid Phase Concentration Using Toluene as Diluent The measurements were made according to experimental procedure 1 described above.

Using toluene as diluent, four series of measurements were made with different starting concentrations of 3-chloropropyne of about 15% by weight, about 22% by weight, about 30% by weight and about 70% by weight. N,N-Diisobutylformamide (DIBF) was also present in the first three series of measurements. The results are shown in tables 1a to 1d. FIG. 1 shows a plot of the vapor pressure [log(p/[hPa])] of 3-chloropropyne for said starting concentrations against the temperature [1/T] and the interpolated curve for a mixture containing about 50% by weight of 3-chloropropyne.

In a fifth series of measurements, mixtures of 3-chloropropyne and toluene of different starting concentrations were prepared, the phase equilibrium at a constant temperature of 50° C. was adjusted according to experimental procedure 1 described above, and the equilibrium proportion of 3-chloropropyne and the total system pressure were determined. The results are shown in table 2. FIG. 2 shows a plot of the equilibrium proportion of 3-chloropropyne in the gas phase and the total system pressure as a function of the equilibrium proportion of 3-chloropropyne in the liquid phase.

TABLE 2

Gas-liquid phase equilibrium of the system 3-chloropropyne/toluene at 50° C.

| Pressure | Equilibrium proportion of 3-chloropropyne | |
|---|---|---|
| p [hPa abs] | x (in the liquid phase) | y (in the gas phase) |
| 123 | 0 | 0 |
| 128 | 0.010 | 0.045 |
| 138 | 0.026 | 0.125 |
| 171 | 0.078 | 0.320 |
| 285 | 0.249 | 0.659 |
| 494 | 0.557 | 0.879 |
| 688 | 0.853 | 0.967 |
| 752 | 0.960 | 0.991 |
| 769 | 0.988 | 0.997 |
| 775 | 0.995 | 0.999 |
| 780 | 1 | 1 |

Example 2

Determination of the Gas Phase Concentration and Vapor Pressure of 3-chloropropyne as a Function of the Liquid Phase Concentration Using n-hexane as Diluent The measurements were made according to experimental procedure 1 described above. Using n-hexane as diluent, mixtures with 3-chloropropyne of different starting concentrations were prepared, the phase equilibrium at a constant temperature of 50° C. was adjusted according to experimental procedure 1 described above, and the equilibrium proportion of 3-chloropropyne and the total system pressure were determined. The results are shown in table 3.

TABLE 3

Gas-liquid phase equilibrium of the system 3-chloropropyne/n-hexane at 50° C.

| Pressure | Equilibrium proportion of 3-chloropropyne | |
|---|---|---|
| p [hPa abs] | x (in the liquid phase) | y (in the gas phase) |
| 541 | 0 | 0 |
| 576 | 0.021 | 0.079 |
| 662 | 0.079 | 0.231 |
| 838 | 0.280 | 0.481 |

TABLE 3-continued

Gas-liquid phase equilibrium of the system 3-chloropropyne/n-hexane at 50° C.

| Pressure | Equilibrium proportion of 3-chloropropyne | |
|---|---|---|
| p [hPa abs] | x (in the liquid phase) | y (in the gas phase) |
| 930 | 0.614 | 0.610 |
| 926 | 0.783 | 0.714 |
| 899 | 0.883 | 0.803 |
| 832 | 0.971 | 0.931 |
| 796 | 0.994 | 0.985 |
| 780 | 1 | 1 |

Example 3

Determination of the Gas Phase Concentration and Vapor Pressure of 3-chloropropyne as a Function of the Liquid Phase Concentration Using Cyclohexane as Diluent The measurements were made according to experimental procedure 1 described above. Using cyclohexane as diluent, mixtures with 3-chloropropyne of different starting concentrations were prepared, the phase equilibrium at a constant temperature of 50° C. was adjusted according to experimental procedure 1 described above, and the equilibrium proportion of 3-chloropropyne and the total system pressure were determined. The results are shown in table 4.

TABLE 4

Gas-liquid phase equilibrium of the system 3-chloropropyne/cyclohexane at 50° C.

| Pressure | Equilibrium proportion of 3-chloropropyne | |
|---|---|---|
| p [hPa abs] | x (in the liquid phase) | y (in the gas phase) |
| 363 | 0 | 0 |
| 389 | 0.015 | 0.082 |
| 469 | 0.063 | 0.266 |
| 673 | 0.256 | 0.561 |
| 782 | 0.527 | 0.691 |
| 822 | 0.759 | 0.787 |
| 805 | 0.967 | 0.953 |
| 790 | 0.993 | 0.989 |
| 780 | 1 | 1 |

Example 4

Determination of the Deflagration Limit of Binary Gas Mixtures Containing 3-chloropropyne The measurements were made according to experimental procedure 2 described above. The hydrocarbon toluene, cyclohexane or n-hexane was used as the second gas component. The measured ranges incapable of deflagration are given in tables 5a to 5c. The measurements show that the type of solvent also has a decisive influence on the position of the deflagration limit.

TABLE 5a

Gas mixture of 3-chloropropyne and toluene

| | 3-Chloropropyne | Toluene |
|---|---|---|
| Incapable of deflagration | ≦71% by volume | ≧29% by volume |

TABLE 5a-continued

Gas mixture of 3-chloropropyne and toluene

| | | |
|---|---|---|
| in the gas phase at 100° C. and 0.1 MPa abs | ≦66.5% by weight | ≧33.5% by weight |

TABLE 5b

Gas mixture of 3-chloropropyne and cyclohexane

| | 3-Chloropropyne | Cyclohexane |
|---|---|---|
| Incapable of deflagration in the gas phase at 100° C. and 0.1 MPa abs | ≦83% by volume ≦81.2% by weight | ≧17% by volume ≧18.8% by weight |

TABLE 5c

Gas mixture of 3-chloropropyne and n-hexane

| | 3-Chloropropyne | n-Hexane |
|---|---|---|
| Incapable of deflagration in the gas phase at 80 to 150° C. and 0.1 MPa abs | ≦80% by volume ≦77.6% by weight | ≧20% by volume ≧22.4% by weight |

Example 5

Determination of the Deflagration Limit of Ternary Gas Mixtures Containing 3-chloropropyne The measurements were made according to experimental procedure 2 described above. Toluene and nitrogen were used as other gas components. The measured gas compositions at which a deflagration can or cannot be triggered are given in tables 6a (for 0.10 MPa abs) and 6b (for 0.19 MPa abs). The deflagration diagrams are shown in FIGS. 3a and 3b. The gas mixture is capable of deflagration within the hatched areas. The measurements prove that the deflagration limit is pressure-dependent.

TABLE 6a

Gas mixture of 3-chloropropyne, toluene and nitrogen at 0.10 MPa abs

| | T [° C.] | 3-Chloropropyne [% by volume] | Toluene [% by volume] | Nitrogen [% by volume] |
|---|---|---|---|---|
| Gas compositions at which a deflagration can be triggered | 100 | 38 | 0 | 62 |
| | 100 | 50 | 6 | 44 |
| | 100 | 60 | 10 | 30 |
| | 100 | 64 | 16 | 20 |
| | 100 | 72 | 28 | 0 |
| Gas compositions at which a deflagration cannot be triggered | 100 | 36 | 0 | 64 |
| | 100 | 48 | 8 | 44 |
| | 100 | 58 | 12 | 30 |
| | 100 | 62 | 18 | 20 |
| | 100 | 70 | 30 | 0 |

TABLE 6b

Gas mixture of 3-chloropropyne, toluene and nitrogen at 0.19 MPa abs

| | T [° C.] | 3-Chloropropyne [% by volume] | Toluene [% by volume] | Nitrogen [% by volume] |
|---|---|---|---|---|
| Gas compositions at which a deflagration can be triggered | 100 | 34 | 0 | 66 |
| | 100 | 54 | 16 | 30 |
| | 120 | 68 | 32 | 0 |
| Gas compositions at which a deflagration cannot be triggered | 100 | 32 | 0 | 68 |
| | 100 | 52 | 18 | 30 |
| | 120 | 66 | 34 | 0 |

Example 6

Semicontinuous Preparation of 3-chloropropyne in Toluene as Diluent (According to the Invention)

250 ml (226.6 g) of a previously mixed solution of 112.2 g of 3-chloropropyne, 11.87 g of N,N-diisobutylformamide (DIBF) and 262 g of toluene were placed in a phosgenation apparatus comprising a multinecked flask with a stirrer and an attached cooling cascade (with a jacketed coil condenser operating at −10° C. and an attached carbon dioxide condenser). The solution thus contained 29.1% by weight of 3-chloropropyne and 67.9% by weight of toluene. The receiver was heated to 50° C. and phosgene gas was introduced. After about 65 g of phosgene had been added, reflux started over the cooling cascade. The metering of 447.3 g (500 ml) of a solution of 103.7 g of propyn-3-ol and 14.6 g of DIBF in 329 g of toluene was started when the phosgene reflux began. The solution was added dropwise over 4 hours and a further 202 g of phosgene gas were introduced in parallel.

During the metering of the solution and the phosgene, an evacuated glass vessel was used to take a sample of the gas phase from the reaction gas space in the multinecked flask up to an internal pressure of 100 hPa abs, atmospheric pressure being restored with nitrogen. Gas chromatographic analysis showed a gas phase composition of approx. 29.5% by volume of carbon dioxide, 0.2% by volume of toluene, 18% by volume of 3-chloropropyne, 19.7% by volume of hydrogen chloride and 32.6% by volume of phosgene.

When the metering had ended, a further 3 g of propyn-3-ol were added over 20 minutes in order to convert the excess phosgene. The reaction mixture was then left to stand for a further 1 hour at 50° C. to allow the post-reaction. According to gas chromatographic analysis, the crude solution formed contained approx. 27% by weight of 3-chloropropyne, corresponding to a crude yield of about 93%.

According to D. R. Forshey et al. in Fire Technology 5 (1969) pages 100 to 111, the addition of 10% by weight of toluene to the liquid phase is already sufficient to stabilize the liquid phase to deflagration up to 4.3 MPa abs, so the liquid phase is also stable to deflagration in the present example.

The gas sample taken during the reaction contained 18% by volume of 3-chloropropyne and 0.2% by volume of toluene. As is evident from the deflagration diagram of FIG. 3a, a ternary gas mixture containing about 18% by volume of 3-chloropropyne and about 0.2% by volume of toluene is well outside the region capable of deflagration, even at 100° C.

The 3-chloropropyne content of 27% by weight in the crude solution obtained corresponds to a proportion x of about 0.31 in the liquid phase. According to the gas-liquid phase equilibrium of the system 3-chloropropyne/toluene at 50° C., measured in example 1, and the plot of FIG. 2 at 50° C., the proportion of 3-chloropropyne in the gas phase is about 0.72 and the cumulative pressure of 3-chloropropyne and toluene is about 330 hPa. This corresponds to a 3-chloropropyne partial pressure of about 238 hPa and a toluene partial pressure of about 92 hPa. As the total system pressure was about 0.1 MPa abs, the gas phase still contained about 0.67 MPa of other gases. These consisted predominantly of the reaction by-products formed, namely hydrogen chloride and carbon dioxide. For a gas mixture with a total pressure of 0.1 MPa abs, the 3-chloropropyne partial pressure of about 238 hPa is equivalent to a proportion of 3-chloropropyne of about 23.8% by volume. The toluene partial pressure present corresponds to a proportion of toluene of about 9.2% by volume.

As is evident from the deflagration diagram of FIG. 3a, a ternary gas mixture containing about 23.8% by volume of 3-chloropropyne and about 9.2% by volume of toluene is well outside the region capable of deflagration, even at 100° C.

Example 7

Semicontinuous Preparation of 3-chloropropyne in Toluene as Diluent (According to the Invention)

400 l of a starting solution consisting of 83.75% by weight of toluene, 15.5% by weight of propyn-3-ol and 0.75% by weight of N,N-diisobutylformamide (DIBF) were placed at a jacket temperature of 30° C. in a phosgenation unit comprising an 8 m$^3$ jacket-heated stirred tank and a cooling cascade (with a first cooling stage at −20° C. and a second cooling stage at −70° C.). 75 l of liquid phosgene were metered in, with stirring, the internal temperature being raised to 48° C. The reaction of the phosgene with propyn-3-ol resulted in the formation of carbon dioxide and hydrogen chloride, which were withdrawn downstream of the cooling cascade as an off-gas stream. When the off-gas stream had subsided, a constant stream of 750 kg/h of starting solution (composition as described above) was introduced from a receiver at a jacket temperature of 50° C. and a constant stream of phosgene was also introduced. The pressure in the reactor was about 0.1 MPa abs. The phosgene feed rate was adjusted in such a way that the internal reactor temperature remained constant at 48° C. The amount of off-gas observed downstream of the cooling cascade during the reaction was about 100 m$^3$/h. The composition of the gas phase before entering the cooling cascade was analyzed by gas chromatography. It contained 33.7% by volume of carbon dioxide, 31.3% by volume of hydrogen chloride, 15% by volume of phosgene, 17% by volume of 3-chloropropyne and 3% by volume of toluene. The temperature of the off-gas before entering the cooling cascade was 35° C.

When the volume in the stirred tank had reached 5.2 m$^3$, the phosgene feed was closed. More starting solution (composition as described above) was subsequently metered in at 48° C. in order to convert any phosgene still dissolved. When the off-gas stream had dropped to 0 m$^3$/h downstream of the cooling cascade, the metering of the starting solution was also stopped and the reaction mixture was left to stand for a further 2 hours at 50° C. to allow the post-reaction. According to gas chromatographic analysis, the crude solution formed contained approx. 19.7% by weight of 3-chloropropyne, corresponding to a crude yield of about 99%. The residual phosgene content was less than 100 ppm by weight.

Since, according to D. R. Forshey et al. in Fire Technology 5 (1969) pages 100 to 111, the addition of 10% by weight of toluene to the liquid phase is already sufficient to stabilize the liquid phase to deflagration up to 4.3 MPa abs, so the liquid phase is also stable to deflagration in the present example.

The 3-chloropropyne content of 19.7% by weight in the crude solution obtained corresponds to a proportion x of about 0.21 in the liquid phase. According to the gas-liquid phase equilibrium of the system 3-chloropropyne/toluene at 50° C., measured in example 1, and the plot of FIG. 2 at 50° C., the proportion of 3-chloropropyne in the gas phase is about 0.60 and the cumulative pressure of 3-chloropropyne and toluene is about 260 hPa. This corresponds to a 3-chloropropyne partial pressure of about 156 hPa and a toluene partial pressure of about 104 hPa. As the total system pressure was about 0.1 MPa abs, the gas phase still contained about 0.74 MPa of other gases. These consisted predominantly of the reaction by-products formed, namely hydrogen chloride and carbon dioxide. For a gas mixture with a total pressure of 0.1 MPa abs, the 3-chloropropyne partial pressure of about 156 hPa is equivalent to a proportion of 3-chloropropyne of about 15.6% by volume. The toluene partial pressure present corresponds to a proportion of toluene of about 10.4% by volume.

As is evident from the deflagration diagram of FIG. 3a, a ternary gas mixture containing about 15.6% by volume of 3-chloropropyne and about 10.4% by volume of toluene is well outside the region capable of deflagration, even at 100° C.

Example 8

Semicontinuous Preparation of 3-chloropropyne in Toluene According to Example 5 of WO 99/46226 (Comparative Example)

In example 5 of WO 99/46226, 22 g of N,N-diisobutylformamide (DIBF) in 70 g of toluene were taken and 112 g of propyn-3-ol and 230 g of phosgene were introduced over 3.5 hours at a constant temperature of 50° C. After a post-reaction time of 1 hour at 50° C., more propyn-3-ol was added in order to convert the excess phosgene. After a further post-reaction time of 1 hour, the reaction product was analyzed by gas chromatography. It contained 65% by weight of 3-chloropropyne.

According to D. R. Forshey et al. in Fire Technology 5 (1969) pages 100 to 111, the addition of 10% by weight of toluene to the liquid phase is already sufficient to stabilize the liquid phase to deflagration up to 4.3 MPa abs, so the liquid phase is also stable to deflagration in the present example.

The 3-chloropropyne content of 65% by weight in the crude solution obtained corresponds to a proportion x of about 0.70 in the liquid phase. According to the gas-liquid phase equilibrium of the system 3-chloropropyne/toluene at 50° C., measured in example 1, and the plot of FIG. 2 at 50° C., the proportion of 3-chloropropyne in the gas phase is about 0.94 and the cumulative pressure of 3-chloropropyne and toluene is about 590 hPa. This corresponds to a 3-chloropropyne partial pressure of about 555 hPa and a toluene partial pressure of about 35 hPa. As the total system pressure was about 0.1 MPa abs, the gas phase still contained about 0.41 MPa of other gases. These consisted predominantly of the reaction by-products formed, namely hydrogen chloride and carbon dioxide. For a gas mixture with a total pressure of 0.1 MPa abs, the 3-chloropropyne partial pressure of about 555 hPa is equivalent to a proportion of 3-chloropropyne of about 55.5% by volume. The toluene partial pressure present corresponds to a proportion of toluene of about 3.5% by volume.

As is evident from the deflagration diagram of FIG. 3a, a ternary gas mixture containing about 55.5% by volume of 3-chloropropyne and about 3.5% by volume of toluene is well inside the region capable of deflagration at 100° C. Thus, under the conditions described in example 5 of WO 99/46226, there is the high safety risk of an uncontrollable deflagration.

Example 9

Semicontinuous Preparation of 3-chloropropyne in Cyclohexane as Diluent (According to the Invention)

151 g of a mixture of 50% by weight (75 g) of 3-chloropropyne, 5% by weight (8 g) of N,N-diisobutylformamide (DIBF) and 45% by weight (68 g) of cyclohexane were placed in a phosgenation apparatus comprising a multinecked flask with a stirrer and an attached cooling cascade (with a jacketed coil condenser operating at −10° C. and an attached carbon dioxide condenser), and were heated to 50° C. At 50° C., 25 g of phosgene gas were metered in over 30 minutes until reflux started. A mixture of 112 g of propyn-3-ol and 15.73 g of DIBF, and 99.34 g of cyclohexane, were then added in parallel from two 250 ml dropping funnels over 3.5 hours at an internal temperature of about 50° C., a further 200 g of phosgene gas being introduced simultaneously.

After a reaction time of 1.5 hours, an evacuated glass vessel was used to take a sample from the reaction gas space up to an internal pressure of 100 hPa abs, atmospheric pressure being restored with nitrogen. Gas chromatographic analysis showed a gas phase composition of approx. 44% by volume of carbon dioxide, 6% by volume of cyclohexane, 18.5% by volume of 3-chloropropyne, 19% by volume of hydrogen chloride and 4.5% by volume of phosgene.

When the metering had ended, a further 10 g of propyn-3-ol were added in order to convert the excess phosgene. The reaction mixture was then left to stand for a further 1.5 hours at 50° C. to allow the post-reaction. According to gas chromatographic analysis, the crude solution formed contained approx. 52% by weight of 3-chloropropyne, 42% by weight of cyclohexane and 6% by weight of DIBF. This corresponds to a crude yield of 3-chloropropyne of about 99%. The gas phase composition of a 50% by weight solution of 3-chloropropyne in cyclohexane is about 69% by volume of 3-chloropropyne and about 31% by volume of cyclohexane at 50° C. Thus the 3-chloropropyne concentration is well below the concentration of 83% by volume measured for the deflagration limit in example 4, table 5b.

Following the above-described experimental procedure for determining the deflagration limit of gas mixtures, an attempt was made to ignite a gas mixture with a composition comparable to that of the abovementioned gas sample. The gas mixture was not ignitable.

The experiment shows that through the addition of cyclohexane, a diluent boiling well below toluene, it is possible to have a 3-chloropropyne concentration of more than 50% by weight in the liquid phase without the gas phase having a composition capable of deflagration during or after the end of the reaction.

Example 10

Semicontinuous Preparation of 3-chloropropyne in Toluene/Pentane as Diluent (According to the Invention)

A solution of 54 g of 3-chloropropyne, 5.72 g of N,N-diisobutylformamide (DIBF), 102.32 g of toluene and 18 g of an n-pentane/isopentane mixture (containing 95% of n-pentane, from Haltermann) was placed in a phosgenation apparatus comprising a multinecked flask with a stirrer and an attached cooling cascade (with a jacketed coil condenser operating at −10° C. and an attached carbon dioxide condenser). The solution thus contained 30% by weight of 3-chloropropyne, 56.8% by weight of toluene and 10% by weight of n-pentane/isopentane mixture. The receiver was heated to 50° C. and 22 g of phosgene gas were introduced. 540 g of a starting solution of 131.68 g of propyn-3-ol and 18.48 g of DIBF in 331.56 g of toluene and 58.32 g of n-pentane/isopentane mixture, and 240 g of phosgene, were then added in parallel over 4 hours at an internal temperature of 50 to 51° C.

During the metering of the solution and the phosgene, an evacuated glass vessel was used to take a sample of the gas phase from the reaction gas space in the multinecked flask up to an internal pressure of 100 hPa abs, atmospheric pressure being restored with nitrogen. Gas chromatographic analysis showed a gas phase composition of approx. 23.3% by volume of carbon dioxide, 0.1% by volume of toluene, 18% by volume of 3-chloropropyne, 18.7% by volume of hydrogen chloride, 33.6% by volume of pentane isomers and 6.3% by volume of phosgene.

When the metering had ended, a further 7.86 g of propyn-3-ol were added in order to convert the excess phosgene. The reaction mixture was then left to stand for a further 2 hours at 50° C. to allow the post-reaction. According to gas chromatographic analysis, the crude solution formed contained approx. 30% by weight of 3-chloropropyne, 56.4% by weight of toluene, 9.6% by weight of pentane isomers and 3.3% by weight of DIBF. This corresponds to a crude yield of 3-chloropropyne of about 99%. The composition of the gas phase above the reaction product at 50° C. was approx. 48% by volume of 3-chloropropyne, 25% by volume of pentane isomers and 24% by volume of toluene.

According to D. R. Forshey et al. in Fire Technology 5 (1969) pages 100 to 111, the addition of 10% by weight of toluene to the liquid phase is already sufficient to stabilize the liquid phase to deflagration up to 4.3 MPa abs, so the liquid phase is also stable to deflagration in the present example.

The composition of the gas phase above the reaction product shows that the proportions of 3-chloropropyne, toluene and pentane isomers are about 0.48, about 0.24 and about 0.25 respectively. It is evident from the deflagration diagram of FIG. 3a that even a ternary gas mixture containing proportions of 3-chloropropyne, toluene and nitrogen of 0.48, 0.24 and 0.28 is well within the region stable to deflagration. As the deflagration-reducing effect of pentane isomers is greater than that of nitrogen due to the higher thermal capacity of pentane isomers compared with nitrogen, the gas phase over the reaction product is even further within the region stable to deflagration than the 3-chloropropyne/toluene/nitrogen gas mixture examined.

Example 11

Semicontinuous Preparation of 3-chloropropyne in Toluene/Methyl Tert-Butyl Ether as Diluent (According to the Invention)

A solution of 54 g of 3-chloropropyne, 5.72 g of N,N-diisobutylformamide (DIBF), 84.32 g of toluene and 36 g of methyl tert-butyl ether (MTBE) was placed in a phosgenation apparatus comprising a multinecked flask with a stirrer and an attached cooling cascade (with a jacketed coil condenser operating at −10° C. and an attached carbon dioxide condenser). The solution thus contained 30% by weight of 3-chloropropyne, 46.8% by weight of toluene and 20% by weight of MTBE. The receiver was heated to 50° C. and 22 g of phosgene gas were introduced. 540 g of a starting solution of 131.68 g of propyn-3-ol and 18.48 g of DIBF in 273.24 g of toluene and 116.64 g of MTBE, and 234 g of phosgene, were then added in parallel over 4 hours at an internal temperature of 50 to 52° C.

During the metering of the solution and the phosgene, an evacuated glass vessel was used to take a sample of the gas phase from the reaction gas space in the multinecked flask up to an internal pressure of 100 hPa abs, atmospheric pressure being restored with nitrogen. Gas chromatographic analysis showed a gas phase composition of approx. 26% by volume of carbon dioxide, 0.03% by volume of toluene, 10.4% by volume of 3-chloropropyne, 31.1% by volume of hydrogen chloride, 2.6% by volume of MTBE and 29.8% by volume of phosgene.

When the metering had ended, a further 3.14 g of propyn-3-ol were added in order to convert the excess phosgene. The reaction mixture was then left to stand for a further 0.5 hour at 50° C. to allow the post-reaction. According to gas chromatographic analysis, the crude solution formed contained approx. 33% by weight of 3-chloropropyne, 45.5% by weight of toluene, 15.6% by weight of MTBE and 3.2% by weight of DIBF. This corresponds to a crude yield of 3-chloropropyne of about 99%. The composition of the gas phase above the reaction product at 50° C. was approx. 53% by volume of 3-chloropropyne, 24% by volume of MTBE and 15% by volume of toluene.

According to D. R. Forshey et al. in Fire Technology 5 (1969) pages 100 to 111, the addition of 10% by weight of toluene to the liquid phase is already sufficient to stabilize the liquid phase to deflagration up to 4.3 MPa abs, so the liquid phase is also stable to deflagration in the present example.

The composition of the gas phase above the reaction product shows that the proportions of 3-chloropropyne, toluene and MTBE are about 0.53, about 0.15 and about 0.24 respectively. It is evident from the deflagration diagram of FIG. 3a that even a ternary gas mixture containing proportions of 3-chloropropyne, toluene and nitrogen of 0.53, 0.15 and 0.32 is well within the region stable to deflagration. As the deflagration-reducing effect of MTBE is greater than that of nitrogen due to the higher thermal capacity of MTBE compared with nitrogen, the gas phase over the reaction product is even further within the region stable to deflagration than the 3-chloropropyne/toluene/nitrogen gas mixture examined.

Example 12

Study of Deflagrability During and After the Synthesis of 3-chloropropyne Using Toluene as Diluent in the Range from 25 to 45% by weight of 3-chloropropyne Under the experimental conditions described in example 6, solutions with a final 3-chloropropyne content of 25% by weight, 30% by weight, 35% by weight, 40% by weight and 45% by weight were prepared, by adjusting the ratio of propyn-3-ol to toluene accordingly, in a 4 l reaction flask in which a high-tension discharger was installed in addition to the construction described. In these syntheses, an ignition spark with an energy of approx. 20 J was created at 10-minute intervals throughout the reaction from the start of phosgene reflux to the end of the experiment.

No deflagration could be triggered in any of the experiments.

TABLE 1a

Gas phase concentration of 3-chloropropyne as a function of the liquid phase concentration using toluene as diluent

| Temperature | | Pressure | Liquid phase | | | Gas phase | | | | |
| --- | --- | --- | --- | --- | --- | --- | --- | --- | --- | --- |
| | | | 3-Chloropropyne | Toluene | DIBF | 3-Chloropropyne | | Toluene | | DIBF |
| T [° C.] | 1/T [$10^{-3}$ 1/K] | p [hPa abs] | [% by weight] | [% by weight] | [% by weight] | [% by weight] | p [hPa] | [% by weight] | p [hPa] | [% by weight] |
| 40.7 | 3.19 | 158 | 15.0 | 84.2 | 0.86 | 53.6 | 85 | 45.8 | 72 | <0.05 |
| 41.3 | 3.18 | 140 | 10.8 | 86.8 | 0.90 | 47.3 | 66 | 52.7 | 74 | <0.05 |
| 59.9 | 3.00 | 346 | 15.3 | 83.6 | 0.91 | 52.0 | 180 | 46.9 | 162 | <0.05 |
| 60.1 | 3.00 | 360 | 17.0 | 81.4 | 0.85 | 55.0 | 198 | 45.2 | 163 | <0.05 |
| 91.7 | 2.74 | 980 | 16.9 | — | 0.87 | 49.5 | 485 | 52.2 | 512 | — |
| 93.1 | 2.73 | 980 | 15.0 | — | 0.92 | 49.0 | 480 | 55.7 | 546 | — |

TABLE 1b

Gas phase concentration of 3-chloropropyne as a function of the liquid phase concentration using toluene as diluent

| Temperature | | Pressure | Liquid phase | | | Gas phase | | | | |
| --- | --- | --- | --- | --- | --- | --- | --- | --- | --- | --- |
| | | | 3-Chloropropyne | Toluene | DIBF | 3-Chloropropyne | | Toluene | | DIBF |
| T [° C.] | 1/T [$10^{-3}$ 1/K] | p [hPa abs] | [% by weight] | [% by weight] | [% by weight] | [% by weight] | p [hPa] | [% by weight] | p [hPa] | [% by weight] |
| 40.0 | 3.19 | 193 | 22.1 | 75.1 | 1.41 | 61.6 | 119 | 35.6 | 69 | <0.05 |
| 40.5 | 3.19 | 210 | 24.4 | 72.7 | 1.31 | 64.5 | 135 | 32.6 | 68 | <0.05 |

TABLE 1b-continued

Gas phase concentration of 3-chloropropyne as a function
of the liquid phase concentration using toluene as diluent

| Temperature | | Pressure | Liquid phase | | | Gas phase | | | | |
| --- | --- | --- | --- | --- | --- | --- | --- | --- | --- | --- |
| | | | 3-Chloropropyne | Toluene | DIBF | 3-Chloropropyne | | Toluene | | DIBF |
| T [°C.] | 1/T [$10^{-3}$ 1/K] | p [hPa abs] | [% by weight] | [% by weight] | [% by weight] | [% by weight] | p [hPa] | [% by weight] | p [hPa] | [% by weight] |
| 59.8 | 3.00 | 417 | 22.9 | 73.8 | 1.44 | 63.0 | 263 | 36.2 | 151 | <0.05 |
| 60.0 | 3.00 | 438 | 24.8 | 72.2 | 1.36 | 65.6 | 287 | 34.0 | 149 | <0.05 |
| 85.1 | 2.79 | 981 | 23.5 | 74.6 | 1.46 | 61.4 | 602 | 38.1 | 374 | <0.05 |
| 86.3 | 2.78 | 981 | 21.5 | 75.8 | 1.55 | 57.6 | 565 | 41.3 | 405 | <0.05 |

TABLE 1c

Gas phase concentration of 3-chloropropyne as a function
of the liquid phase concentration using toluene as diluent

| Temperature | | Pressure | Liquid phase | | | Gas phase | | | | |
| --- | --- | --- | --- | --- | --- | --- | --- | --- | --- | --- |
| | | | 3-Chloropropyne | Toluene | DIBF | 3-Chloropropyne | | Toluene | | DIBF |
| T [°C.] | 1/T [$10^{-3}$ 1/K] | p [hPa abs] | [% by weight] | [% by weight] | [% by weight] | [% by weight] | p [hPa] | [% by weight] | p [hPa] | [% by weight] |
| 40.1 | 3.19 | 225 | 29.5 | 67.0 | 1.60 | 71.9 | 162 | 27.6 | 62 | <0.05 |
| 40.3 | 3.19 | 215 | 27.3 | 69.2 | 1.69 | 69.0 | 148 | 30.4 | 65 | <0.05 |
| 59.9 | 3.00 | 473 | 29.2 | 67.8 | 1.66 | 70.3 | 333 | 29.3 | 139 | <0.05 |
| 60.1 | 3.00 | 495 | 30.2 | 65.7 | 1.60 | 71.8 | 355 | 27.6 | 137 | <0.05 |
| 80.7 | 2.83 | 979 | 29.8 | 65.8 | 1.68 | 68.1 | 667 | 31.1 | 304 | <0.05 |
| 81.3 | 2.82 | 979 | 29.4 | 67.8 | 1.83 | 67.6 | 662 | 31.4 | 307 | <0.05 |

TABLE 1d

Gas phase concentration of 3-chloropropyne as a function
of the liquid phase concentration using toluene as diluent

| Temperature | | Pressure | Liquid phase | | | Gas phase | | | | |
| --- | --- | --- | --- | --- | --- | --- | --- | --- | --- | --- |
| | | | 3-Chloropropyne | Toluene | DIBF | 3-Chloropropyne | | Toluene | | DIBF |
| T [°C.] | 1/T [$10^{-3}$ 1/K] | p [hPa abs] | [% by weight] | [% by weight] | [% by weight] | [% by weight] | p [hPa] | [% by weight] | p [hPa] | [% by weight] |
| 20 | 3.41 | 168 | 70.0 | 30.0 | — | 93.9 | 157 | 6.1 | 10 | — |
| 50 | 3.09 | 572 | 69.2 | 30.8 | — | 92.6 | 530 | 7.4 | 42 | — |
| 68.9 | 2.92 | 1100 | 69.2 | 30.8 | — | 91.0 | 1001 | 9.0 | 99 | — |

We claim:

1. A method for the intrinsically safe handling of 3-chloropropyne in the presence of a diluent with a boiling point ranging from −50° C. (223 K) to 200° C. (473 K) under atmospheric pressure, wherein a diluent boiling at the same temperature as 3-chloropropyne or above is used in an amount of 50 to 2,000% by weight in the liquid phase, based on the amount of 3-chloropropyne in the liquid phase, and the concentration of 3-chloropropyne in the liquid phase and in the gas phase is kept below the concentrations capable of deflagration by means of the type and amount of the diluent, the temperature and the total system pressure.

2. A method as claimed in claim 1 wherein a diluent boiling at the same temperature as 3-chloropropyne or above is used in an amount of 50 to 1 000% by weight in the liquid phase, based on the amount of 3-chloropropyne in the liquid phase.

3. A method as claimed in claim 1 wherein the diluent used, which boils at the same temperature as 3-chloropropyne or above, is an unbranched or branched $C_6$- to $C_8$-alkane, an unbranched or branched $C_6$- to $C_8$-cycloalkane with a 5-membered or 6-membered ring, benzene, toluene, ethylbenzene, xylenes or mixtures thereof.

4. A method as claimed in claim 1 wherein a mixture of (a) a diluent boiling at the same temperature as 3-chloropropyne or above, and (b) a diluent boiling below 3-chloropropyne, is used.

5. A method as claimed in claim 4 wherein the diluent (a) used, which boils at the same temperature as 3-chloropropyne or above, is an unbranched or branched $C_6$- to $C_8$-alkane, an unbranched or branched $C_6$- to $C_8$-cycloalkane with a 5-membered or 6-membered ring, benzene, toluene, ethylbenzene, xylenes or mixtures thereof, and the diluent (b) used, which boils below 3-chloropropyne, is a $C_3$- to $C_5$-alkane, cyclopentane, an aliphatic ether having a total of 2 to 5 carbon atoms, chloromethane or mixtures thereof.

6. A method as claimed in claim 1 wherein the pressure balance between the total system pressure and the partial pressure of 3-chloropropyne and the partial pressure of the diluent is compensated by the presence of an inert gas.

7. A method as claimed in claim 1 wherein the system is kept at a temperature ranging from 0 to 100° C. and at a total pressure ranging from 0.05 to 0.5 MPa abs.

8. A method as claimed in claim 1 wherein the 3-chloropropyne is stored or transported.

9. A method as claimed in claim 1 wherein the 3-chloropropyne is prepared by reacting propyn-3-ol with a chlorinating agent in the presence of a catalyst.

10. A method as claimed in claim 9 wherein the chlorinating agent used is phosgene and the catalyst used is an N,N-disubstituted formamide of the general formula (I):

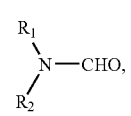

in which $R^1$ and $R^2$ independently of one another are $C_1$- to $C_8$-alkyl or $R^1$ and $R^2$ together are a $C_4$- or $C_5$-alkylene chain which can optionally be interrupted by one or more oxygen or nitrogen atoms.

11. Dyestuffs, pharmaceutical and agricultural active ingredients, electroplating auxiliaries, disinfectants, steroids and growth hormones comprising the 3-chloropropyne as defined in claim 1.

* * * * *